United States Patent
Mansour et al.

(10) Patent No.: US 8,715,247 B2
(45) Date of Patent: May 6, 2014

(54) COLLAPSIBLE VALVE

(75) Inventors: George M. Mansour, Pomona, CA (US); James Bennett, Corona, CA (US)

(73) Assignee: Carefusion 303, Inc., San Diego, CA (US)

( * ) Notice: Subject to any disclaimer, the term of this patent is extended or adjusted under 35 U.S.C. 154(b) by 57 days.

(21) Appl. No.: 12/512,719

(22) Filed: Jul. 30, 2009

(65) Prior Publication Data
US 2011/0028914 A1 Feb. 3, 2011

(51) Int. Cl.
*A61M 5/00* (2006.01)

(52) U.S. Cl.
USPC .......................................................... 604/246

(58) Field of Classification Search
USPC ................... 604/249, 246; 251/149.6
See application file for complete search history.

(56) References Cited

U.S. PATENT DOCUMENTS

| | | | |
|---|---|---|---|
| 5,730,418 A | 3/1998 | Feith et al. | |
| 5,782,816 A | 7/1998 | Werschmidt et al. | |
| 7,184,825 B2 | 2/2007 | Leinsing et al. | |
| 2006/0025724 A1 | 2/2006 | Chen | |
| 2006/0027270 A1* | 2/2006 | Truitt et al. | 137/843 |

FOREIGN PATENT DOCUMENTS

CN 1139010 A 1/1997

OTHER PUBLICATIONS

International Search Report and Written Opinion issued for PCT/US2010/24875, dated Apr. 28, 2010, 7 pages.
Max Plus Brochure, http://www.maximusmedical.com/pdf/maxPlus_Brochure.pdf (last accessed Jul. 29, 2009), 2 pages, Medegen, Inc.
Max Plus Clear Brochure, http://www.maximusmedical.com/pdf/MaxPlusClearNewFlyer.pdf (last accessed Jul. 29, 2009), 2 pages, Medegen, Inc.
Garcia, R. et al., "A Study of the Effects on Bacteremia and Sharps Injury Rates after Introduction of an Advanced Luer Activated Device (LAD) for Intravascular Access in a Large Hospital Setting," http://www.maximusmedical.com/pdf/Garciac%20Study.pdf (last accessed Jul. 29, 2009), 6 pages, Medegen, Inc.
Search Report for Chinese Patent Application No. 2010800386308 dated Feb. 22, 2013.

\* cited by examiner

*Primary Examiner* — Kevin C Sirmons
*Assistant Examiner* — Deanna K Hall
(74) *Attorney, Agent, or Firm* — McDermott Will & Emery LLP (57) ABSTRACT

A collapsible valve comprising a first portion with at least one dimple in a side thereof, and a second portion, the second portion being narrower than the first portion and arranged along an axial dimension of the first portion, the second portion including a cut therein.

10 Claims, 9 Drawing Sheets

FIG. 9C ized, forming a septum, and including at least one dimple thereon. The dimple is angularly offset from the cut by approximately ninety degrees, enough so that a load point on the top surface of the valve is shifted away from the cut to delay the collapse of the cut and result in less forward fall of the top portion when the cut collapses. A method according to one embodiment is related to processes for manufacture of needleless access devices. Another embodiment is directed to a needleless access device that includes a collapsible valve.

COLLAPSIBLE VALVE

TECHNICAL FIELD

The present disclosure relates, generally, to fluid flow devices and, more specifically, to valves for use in medical devices.

BACKGROUND OF THE INVENTION

Figure 1:
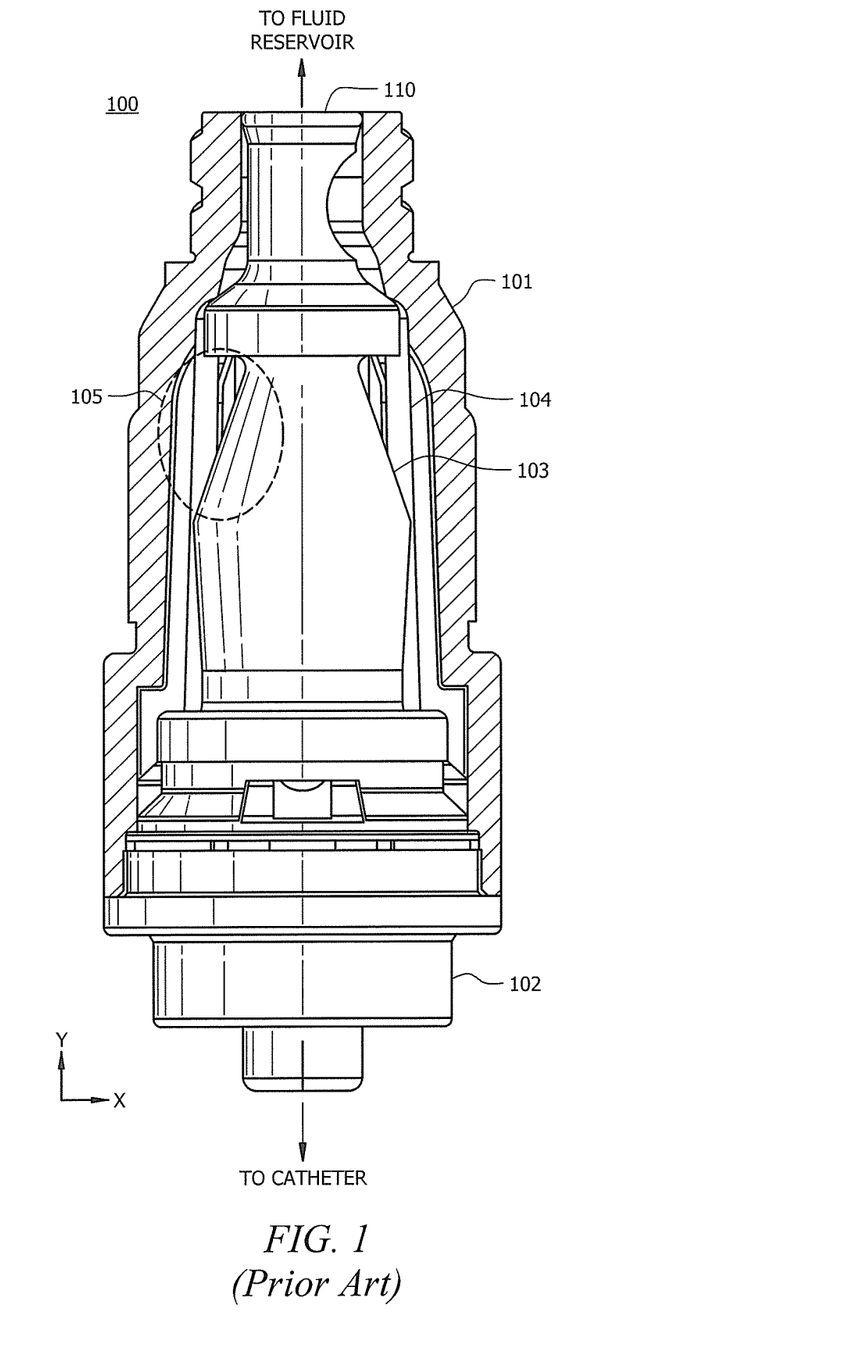
FIG. 1 is a cut-away view of a current needleless access device.

Needleless access devices allow a healthcare professional to, e.g., replace/add IV bags, and/or access an IV line without having to use a needle. FIG. 1 is a cut-away view of a current needleless access device 100. Needleless access device 100 includes female luer fitting 101, male luer fitting 102, and valve 103. When in use, male luer fitting 102 is connected to, e.g., a catheter or to a female luer, and female luer fitting 101 is connected to a fluid reservoir. Female luer fitting 101 is connected to the fluid reservoir via a second male luer fitting (not shown) that includes a hollow member inserted through the top of female luer fitting 101, collapsing valve 103 down into volume 104 to break the seal and create a fluid flow path. The hollow member of the second male luer fitting delivers the fluid, which flows around valve 103 into channels (not shown) in male luer fitting 102 and into the catheter or female luer.

Inside valve 103 is a gap (or septum, not shown), that is filled with air. Device 100 is a positive displacement device, so that when a new connection is made at female luer fitting 101, device 100 pulls fluid in from the male side of the valve (i.e., the side proximate male luer fitting 102). When a disconnection is made at female luer fitting 101, device 100 pushes fluid in from the female side (i.e., the side proximate the top of female luer fitting 101. The advantage of positive displacement is that when a disconnection is made, device 100 expels fluid out of the male luer fitting 102 and effectively flushing the catheter. By contrast, many devices on the market today have negative displacement, so that when a syringe is disconnected, such device pulls a little bit of fluid from the male luer side, which, if a catheter is being used, means that blood is pulled into the catheter lumen. Blood that is left in a catheter lumen may clot and cause health problems for the patient.

An additional feature of device 100 is that when the female end is accessed by a male luer (not shown), valve 103 is elastic so that it can bend out of the way to allow flow and then return to its original shape after a disconnection is made at the female end. Thus, device 100 re-seals itself and forms a flat surface that can be disinfected at the top surface 110 using an alcohol swab. By contrast, many devices on the market use plastic valves that cannot flex to move out of the way to allow flow, thus requiring the use of valves that are slanted or incorporating features at the top, making swabbing difficult.

Device 100 has a symmetrical valve body providing symmetrical wall strength, as well as weakness points on both sides by virtue of duckbills 105. Furthermore, device 100 includes uniform wall thickness in the valve body, even at and around duckbills 105. The contact area between a luer and the top surface 110 of valve 103 and the type of luer motion will dictate the form of collapse of the valve body. Device 100 provides good performance, but could benefit from enhanced repeatability and controllability of collapse.

BRIEF SUMMARY OF THE INVENTION

Various embodiments of the invention are directed to valves, and to needleless access devices that use collapsible valves, which include a cut and at least one dimple to cause specific collapsing valve behavior. In one specific example, a cut is placed on a top portion of a valve, the top portion being narrower in diameter than a bottom portion and forming the top seal of a needleless access device. The bottom portion is substantially cylindrical, forming a septum, and including at least one dimple thereon. The dimple is angularly offset from the cut by approximately ninety degrees, enough so that a load point on the top surface of the valve is shifted away from the cut to delay the collapse of the cut and result in less forward fall of the top portion when the cut collapses. A method according to one embodiment is related to processes for manufacture of needleless access devices. Another embodiment is directed to a needleless access device that includes a collapsible valve.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 2A:
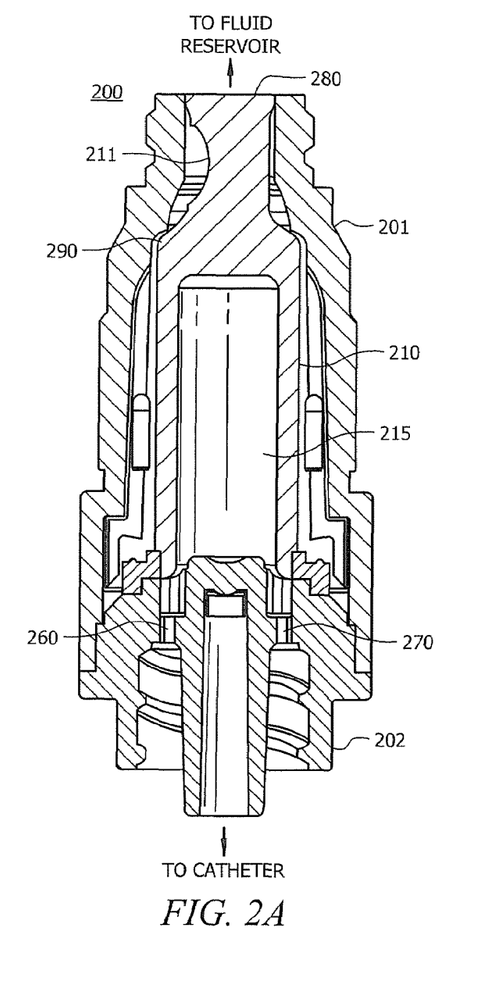
FIGS. 2A and 2B are cut-away views showing an exemplary needleless access device adapted according to one embodiment of the invention.
Figure 2B:
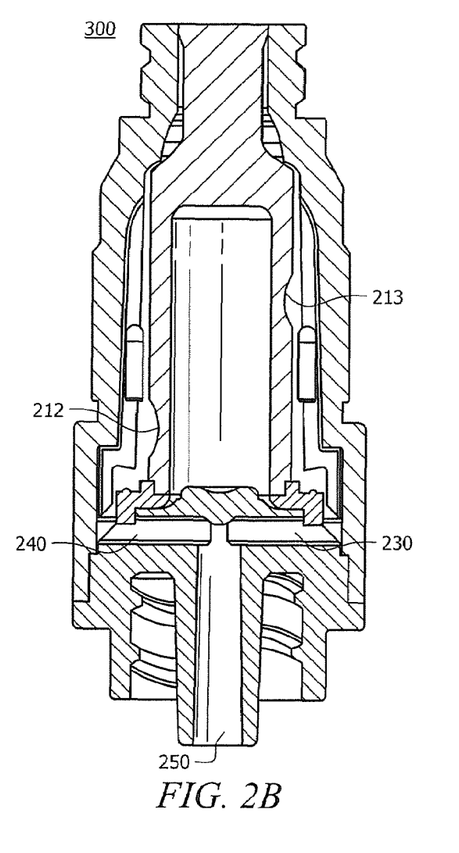

FIGS. 2A and 2B are cut-away views showing exemplary needleless access device 200 adapted according to one embodiment of the invention. The view in FIG. 2B is rotated ninety degrees from that shown in FIG. 2A.

Device 200 includes female luer fitting 201, male luer fitting 202, and valve 210. Valve 210 includes cut 211, which in this example, is referred to as a "smiley cut." Valve 210 also includes dimples 212 and 213 on the outside of its lower portion and placed with axial and angular offsets from each other so that the body of valve 210 is not symmetrical. While cut 211 is referred to as a cut, it can be manufactured using any of a variety of techniques, including molding so that a cut is not actually made. An example of a material that may be used for male and female luer fittings 201 and 202 is polycarbonate, and an example of a material that may be used for valve 210 is silicone, though any of a variety of suitable materials may also be used in various embodiments.

Device 200 provides for positive displacement and self sealing, similar to the device shown in FIG. 1. Male luer fitting 202 at the bottom, connects to a catheter or other medical device (not shown) that is connected to the body of the patient. A syringe (not shown) mates with female luer fitting 201 to collapse valve 210 into the cavity defined between male and female luer fittings 201 and 202. Fluid flow goes from the top of device 200, around valve 210, and through channels 230, 240 to middle channel 250 of male luer fitting 202. Valves 260 and 270 allow air to enter and escape septum 215 of valve 210.

When closed, valve 210 provides two seals. The first seal is at the top surface 280 of device 200. The second seal is at shoulder 290. As explained in more detail with respect to FIG. 5, insertion of a syringe at female luer fitting 201 collapses valve 210, thereby breaking the seals. Valve 210 acts as a spring, so that when it is pushed it down, it collapses, and when the force is removed, it returns to its shape thereby resealing. Generally, the thicker the wall of valve 210, the more spring force, and the thinner the wall, the less spring force. Therefore, wall thickness affects characteristics, such as ease of syringe insertion and displacement. In one particular example where valve 210 is approximately two centimeters in length, a wall thickness within the range of 0.030 and 0.038 inches provides acceptable displacement, sealing, and ease of use. Of course, at dimples 212 and 213 the wall thickness is less, as can be seen especially well at FIG. 3A.

In one example, device 200 is manufactured by separately molding valve 210 and male and female luer fittings 201 and 202. Valve 210 is then placed in the cavity that is formed by male and female luer fittings 201 and 202. Male and female luer fittings 201 and 202 are positioned and welded. Device 200 is then sterilized and packaged. Other methods for manufacturing are possible, e.g., by gluing rather than welding male and female luers 201 and 202, and are within the scope of embodiments.

Figure 3A:
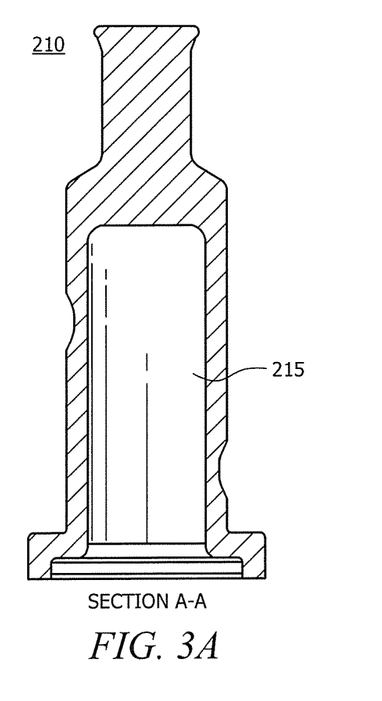
FIGS. 3A-C show views of a valve by itself.
Figure 3B:
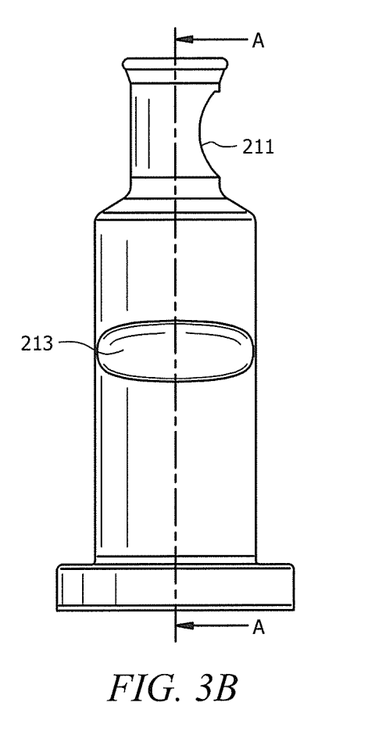
Figure 3C:
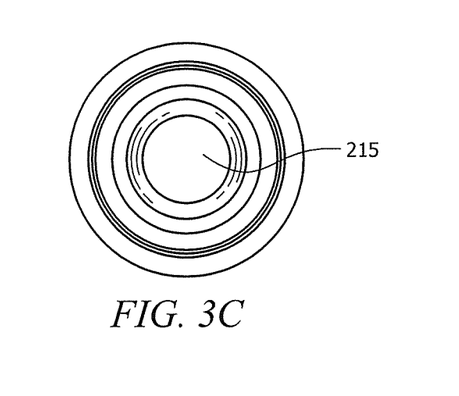
Figure 4A:
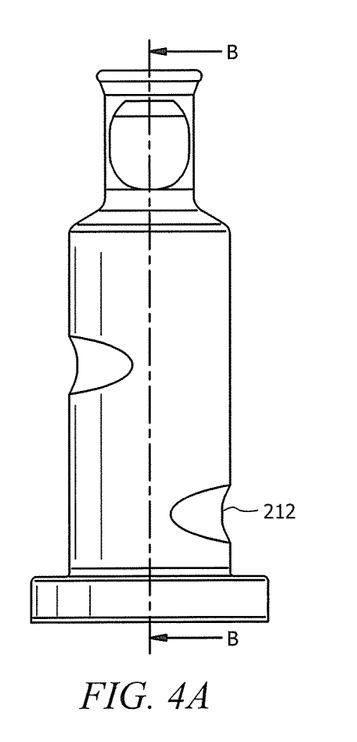
FIGS. 4A and 4B show views ninety degrees from those of FIGS. 3A and 3B.
Figure 4B:
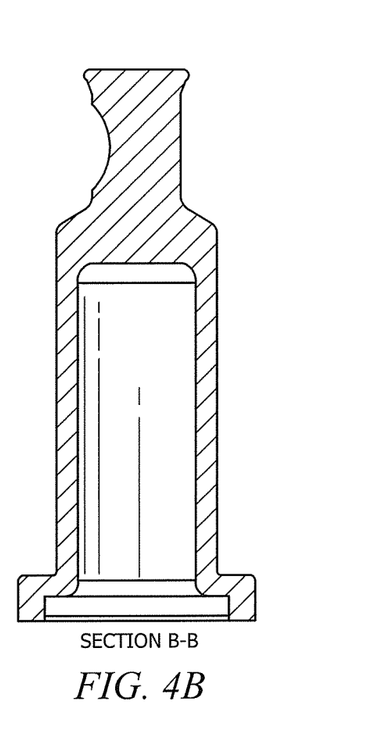

FIGS. 3A-C show views of valve 210 by itself. FIG. 3B shows a side view, FIG. 3A shows a cut-away view, and FIG. 3C shows a bottom view of valve 210. As can be seen, both the top portion and the bottom portion of valve 210 are annular (in this case, substantially cylindrically shaped), where the top portion includes smiley cut 211, and the bottom portion includes dimples 212 and 213. The bottom portion of valve 210 is substantially hollow, defining septum 215. FIGS. 4A and 4B show views ninety degrees from those of FIGS. 3A and 3B.

Figure 5:
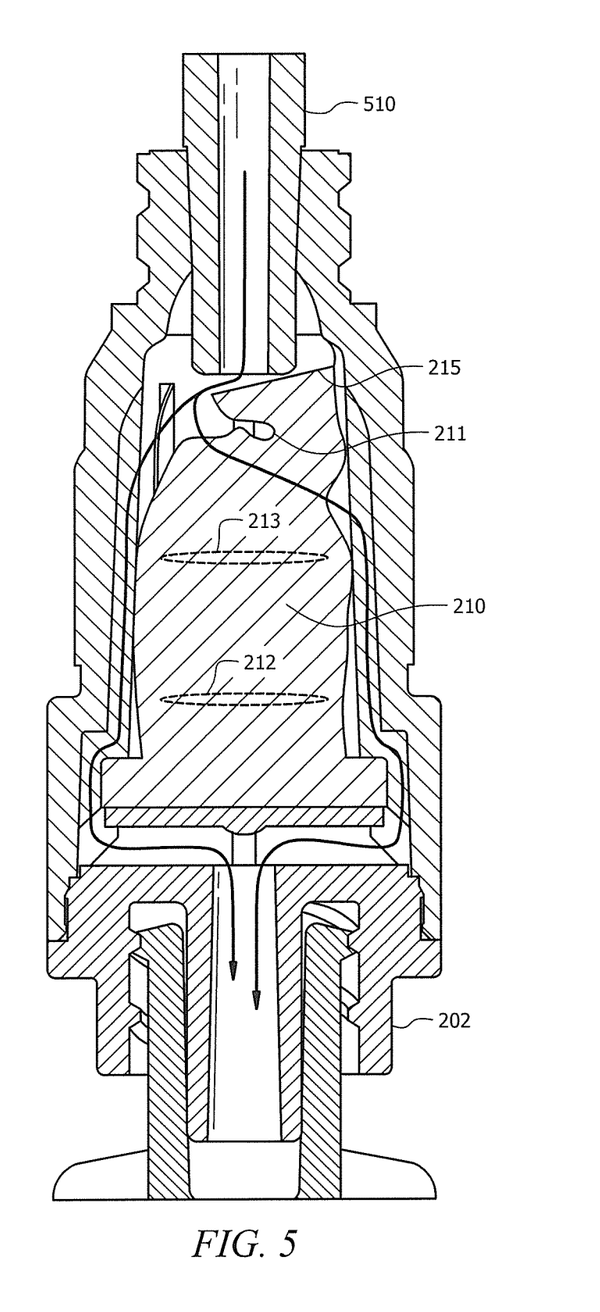
FIG. 5 is an illustration of an exemplary needleless access device with a syringe inserted therein and collapsing an exemplary valve.
Figure 6A:
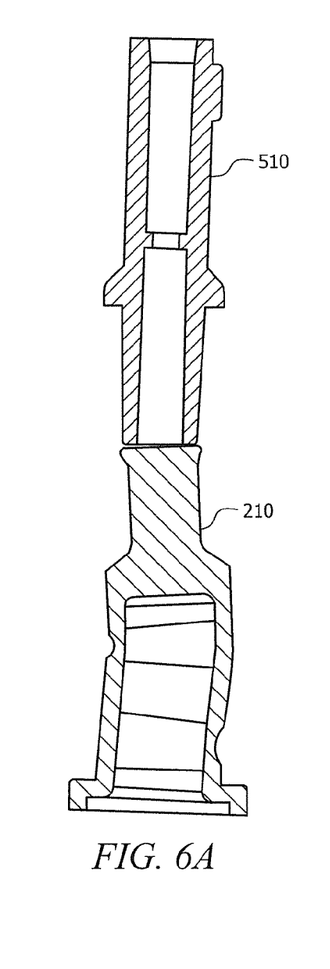
FIGS. 6A-6D illustrate the behavior of an exemplary valve, as pressure is applied by a syringe, but before collapse, according to embodiments of the invention.
Figure 6B:
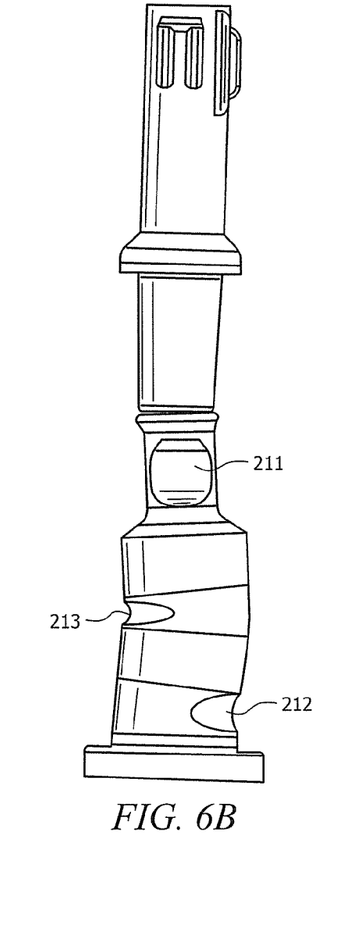
Figure 6C:
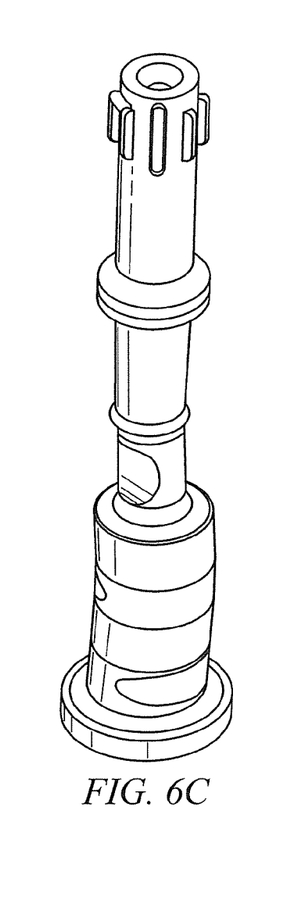
Figure 6D:
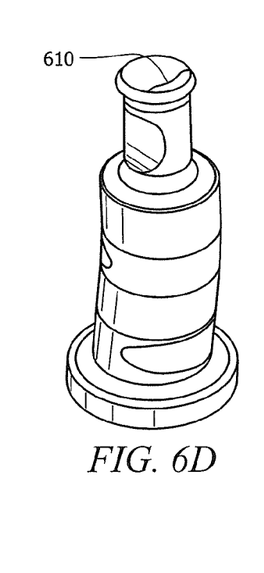

FIG. 5 is an illustration of exemplary device 200 with exemplary syringe 510 inserted therein and collapsing valve 210. Smiley cut 211 collapses, tilting its top surface 216 to let fluid flow out of syringe 510. The lower portion of valve 210 also collapses, aided by dimples 212 and 213, which act as two weak points, placed to cause the lower portion to collapse before smiley cut 211 collapses. Arrows are added to FIG. 5 to illustrate a path of fluid as it flows through syringe 510, around valve 210, and out of male luer 202.

In the embodiments shown in FIGS. 2-5, smiley cut 211 is placed relative to dimples 212 and 213 to facilitate specific collapsing behavior. FIGS. 6A-6D illustrate the behavior of valve 210, as pressure is applied by syringe 510, but before collapse. In the embodiment of FIGS. 2-6, dimple 213 is placed ninety degrees clockwise from smiley cut 211, which places load point 610 counterclockwise to smiley cut 211 (wherein clockwise and counterclockwise refer to the orientation shown in FIGS. 2-6, where the valve 210 is shown with smiley cut 211 above the dimples). The placement of load point 610 is notable because a male luer fitting (not shown) associated with syringe 510 has a thread to connect to female luer fitting 201, thereby rotating syringe 510 as it is inserted (and in turn, putting rotational pressure on valve 210). As dimple 213 begins to collapse, pressure point 610 appears ninety degrees from smiley cut 211, where the side of the top portion of valve 210 is stronger than it is directly above smiley cut 211. In this embodiment, smiley cut 211 collapses later than it would in a scenario where load point 610 is placed directly over smiley cut 211.

Figure 7A:
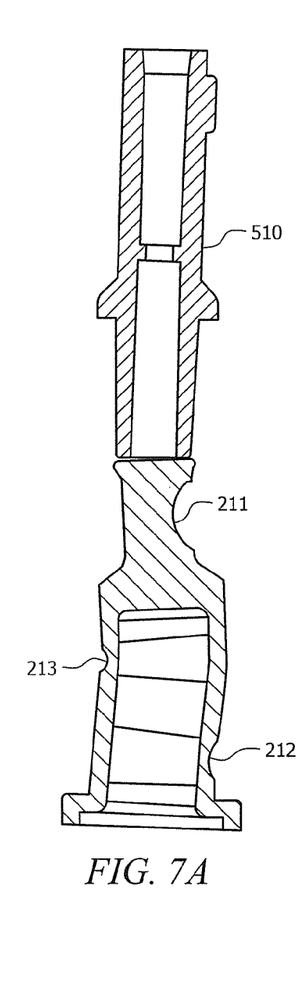
FIGS. 7A-7D illustrate behavior of an exemplary valve as pressure is applied by a syringe, but before collapse, according to embodiments of the invention.
Figure 7B:
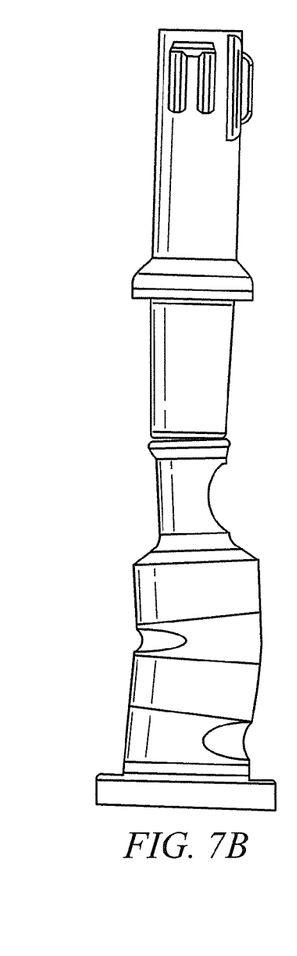
Figure 7C:
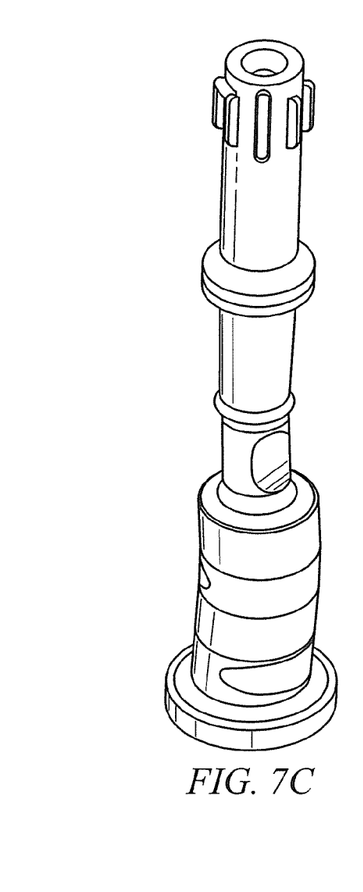
Figure 7D:
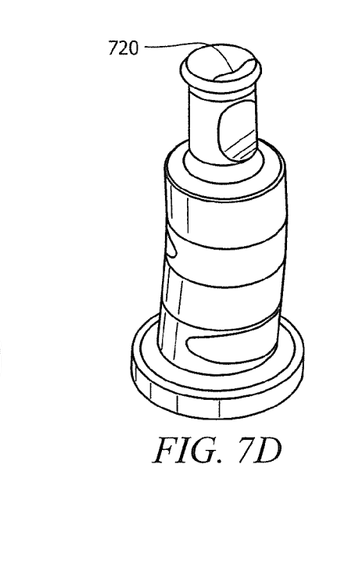

By contrast, FIGS. 7A-7B illustrate behavior of valve 710 as pressure is applied by syringe 510, but before collapse, according to embodiments of the invention. In valve 710, smiley cut 211 is 180 degrees from dimple 213 and directly above dimple 212. Such placement of dimples 212, 213 and smiley cut 211 causes pressure point 720 to be directly above smiley cut 211, thereby causing smiley cut 211 to collapse sooner than it does in the scenario illustrated in FIGS. 6A-6D.

Figure 8:
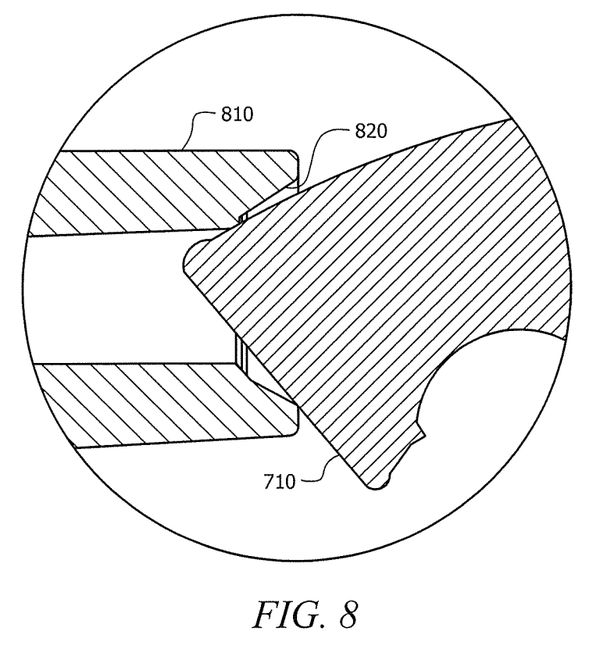
FIG. 8 is an illustration of one scenario of use of an exemplary valve.

In many uses, both valve 210 and valve 710 are acceptable alternatives. However, in scenarios wherein syringe 510 includes a counterbore, early collapse of smiley cut 211 may cause the top of valve 710 to fall forward and become lodged in the counterbore, thereby somewhat impeding the flow of fluid. Such a scenario is shown in FIG. 8, where the top of valve 710 is lodged in counterbore 820 of syringe 810. By contrast, valve 210 delays the collapse of smiley cut 211, providing a more vertical collapse of smiley cut 211 and avoiding blockage of syringe counterbores. Thus, in scenarios where a syringe includes a counterbore, valve 210 can be employed successfully. Both valve 210 and valve 710 can be successfully employed in applications using a syringe, such as that shown in FIGS. 5-7. Various embodiments can use any angular displacement of a dimple relative to a cut, with valve 210 and valve 710 illustrating two examples.

Figure 9A:
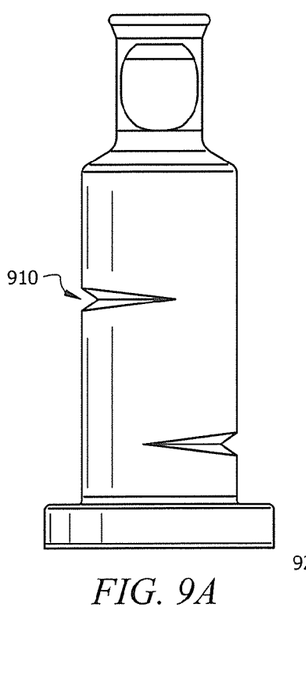
FIG. 9 shows three examples of a wide variety of cuts that can be applied to some embodiments of the invention.
Figure 9B:
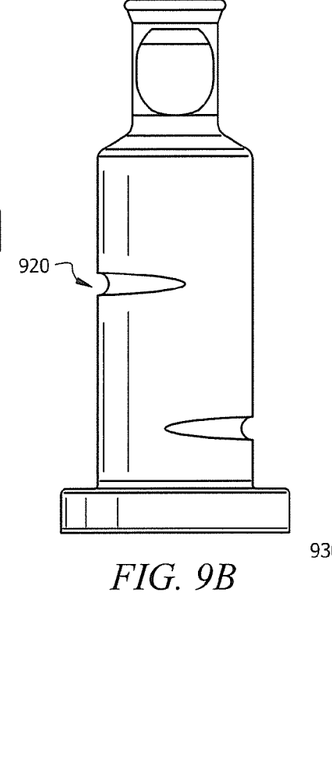
Figure 9C:
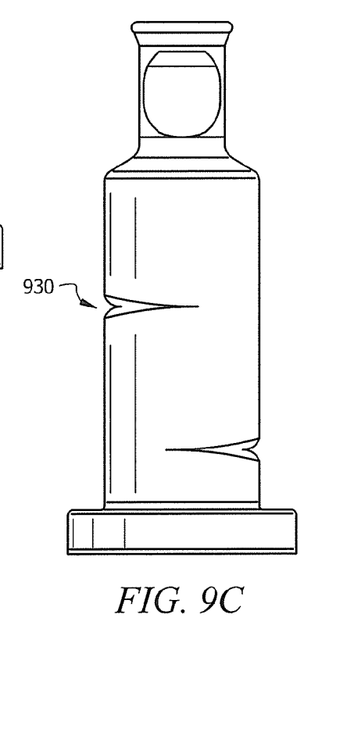

While valves 210 and 710 are shown with two dimples each, various embodiments are not so limited. For instance, more dimples may be added, and some embodiments may include only one dimple. Furthermore, embodiments are not limited to the use of smiley cuts, as other shaped cuts may be employed. For instance, FIGS. 9A-9C show V-cut 910, U-cut 920, and "seagull" cut 930, which are but three examples of a wide variety of cuts that can be applied to embodiments.

As shown above, various embodiments include valves with flat tops that facilitate flow around, rather than through, said valves. Such features provide advantages over embodiments that use hard plastic, do not have flat tops, and/or allow flow through, rather than around valves. For instance, valves 210 and 710 of the embodiments described above provide positive displacement and are self-flushed, thereby providing better hygiene that negative displacement devices. Furthermore, the flat top surfaces of valves 210 and 710 can provide for better swabability than do devices with slanted or grooved tops, once again providing better hygienic qualities. Additionally, the dimples and cuts shown in the embodiments above provide for somewhat predictable collapse of the valves, and (especially in the case of valve 210) applicability to any of a variety of syringes.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A needleless access device comprising:
    a housing having an interior cavity;
    a valve disposed within the interior cavity, the valve comprising:
        a hollow first portion comprising at least one side cut; and
        a second portion fixedly coupled to the first portion, the second portion comprising a side cut;
    wherein the first and second portions each separately collapse when the access device is actuated by a needleless connector such that the valve moves from a sealed position to an open position, and wherein the at least one side cut in the first portion is approximately 90 degrees from the cut in the second portion such that the first portion collapses before the second portion collapses as the needleless connector actuates the access device.

2. The needleless access device of claim 1, wherein the first portion further comprises a cavity with a cylindrical wall, the at least one side cut being formed in the cylindrical wall.

3. The needleless access device of claim 2, wherein the cylindrical wall has a thickness that is selected to cooperate with the at least one side cut to cause the first portion to collapse before the second portion collapses as the needleless connector actuates the access device.

4. The needleless access device of claim 2, wherein the cavity of the first portion is sealed to the housing to form a liquid space between the housing and the valve and a separate air space within the cavity of the first portion.

5. The needleless access device of claim 4, wherein the air space is vented by a passage through the housing to the outside environment.

6. The needleless access device of claim 4, wherein a volume of the air space is reduced and a volume of the liquid space increased as the valve moves from the sealed position to the open position.

7. The needleless access device of claim 1, wherein the at least one side cut of the first portion is positioned clockwise relative to the side cut of the second portion.

8. The needleless access device of claim 1, wherein no side cut of the first portion is positioned under the side cut of the second portion.

9. The needleless access device of claim 1, wherein the second portion further comprises a flat surface that is positioned substantially flush with an inlet opening in the housing when the valve is in the sealed position and is displaced from the inlet opening when the valve is in the open position.

10. A needleless access device comprising:
    a lower housing having an outlet;
    an upper housing sealingly coupled to the lower housing to form an interior cavity, the upper housing having an inlet;
    a valve disposed within the interior cavity, the valve comprising:
        a first portion comprising a closed-end cylindrical wall that forms a cavity, the cylindrical wall having a perimeter and at least two side cuts on opposite sides of an outside surface of the cylindrical wall; and
        a solid second portion fixedly coupled to and aligned with the first portion, the second portion comprising a smiley cut and a flat top surface, wherein the smiley cut is positioned at 90 degrees from the side cuts of the first portion;
    wherein the perimeter of the cylindrical wall is sealed to the lower housing so as to form a liquid space between the valve and the coupled upper and lower housings and an air space within the cavity of the first portion, the air space being vented to the external environment through a passage on the lower housing, and wherein the first portion collapses before the second portion collapses as the access device is actuated by a needleless connector such that the valve moves from a sealed position to an open position.

\* \* \* \* \*